United States Patent [19]

Yamamoto et al.

[11] Patent Number: 5,102,623

[45] Date of Patent: Apr. 7, 1992

[54] INFINITESIMAL LIQUID REACTOR

[75] Inventors: Tomoo Yamamoto; Shigeki Yagi; Munechika Sakabe; Osamu Segawa; Kiyoshi Kobayashi, all of Tokyo, Japan

[73] Assignee: Seiko Instruments, Inc., Tokyo, Japan

[21] Appl. No.: 255,474

[22] Filed: Oct. 11, 1988

[30] Foreign Application Priority Data

| Oct. 9, 1987 [JP] | Japan | 62-254901 |
|---|---|---|
| Oct. 9, 1987 [JP] | Japan | 62-254902 |
| Nov. 6, 1987 [JP] | Japan | 62-280420 |
| Jan. 13, 1988 [JP] | Japan | 63-5463 |

[51] Int. Cl.⁵ ............................................. G01N 35/00
[52] U.S. Cl. ........................................ 422/63; 422/65; 422/100; 436/47; 436/48; 436/180; 73/864.24; 73/864.25; 141/130
[58] Field of Search .................. 422/63, 65, 100; 436/47, 48, 180; 73/864.24, 864.25; 141/130

[56] References Cited

U.S. PATENT DOCUMENTS

| Re. 27,756 | 9/1973 | Martin . | |
|---|---|---|---|
| 3,650,306 | 3/1972 | Lancaster | 141/238 |
| 3,770,591 | 9/1973 | Boirat | 435/809 X |
| 4,478,094 | 10/1984 | Salomaa et al. | 73/863.22 |

FOREIGN PATENT DOCUMENTS

| 0230162 | 12/1984 | Japan | 436/47 |
|---|---|---|---|
| 8602168 | 4/1986 | PCT Int'l Appl. . | |
| 8700083 | 1/1987 | PCT Int'l Appl. . | |
| 8706008 | 10/1987 | PCT Int'l Appl. . | |
| 1528424 | 10/1978 | United Kingdom . | |

Primary Examiner—Robert J. Warden
Assistant Examiner—Stephanie Blythe
Attorney, Agent, or Firm—Spensley Horn Jubas & Lubitz

[57] ABSTRACT

An automatic infinitesimal liquid reactor equipped with a pipetter for dispensing reagents employs two stages which are capable of sliding horizontally. A microplate which has a plurality of recesses in rows is placed in one stage and reagent bottles are placed on the other stage. The pipetter is supported on a horizontal guide rail operating slidably horizontally and along an axis perpendicular to the direction in which the two stages slide. The horizontal guide rail is supported on a vertical guide rail so as to operate slidably in a vertical direction. Thus the pipetter can be moved in a plane perpendicular to the direction in which the two stages slide. When reagents are sucked from reagent bottles, the second stage is slid so that a reagent bottle is superposed below the pipetter and the pipetter is moved downwardly into the reagent bottle to draw in a reagent. When the reagent is discharged, the first stage is slid so that the microplate is superposed below the pipetter and the pipetter is moved downwardly into a recess to discharge the reagent, thereby dispensing a reagent efficiently and minimizing the space required for the reactor.

6 Claims, 6 Drawing Sheets

F I G. 10
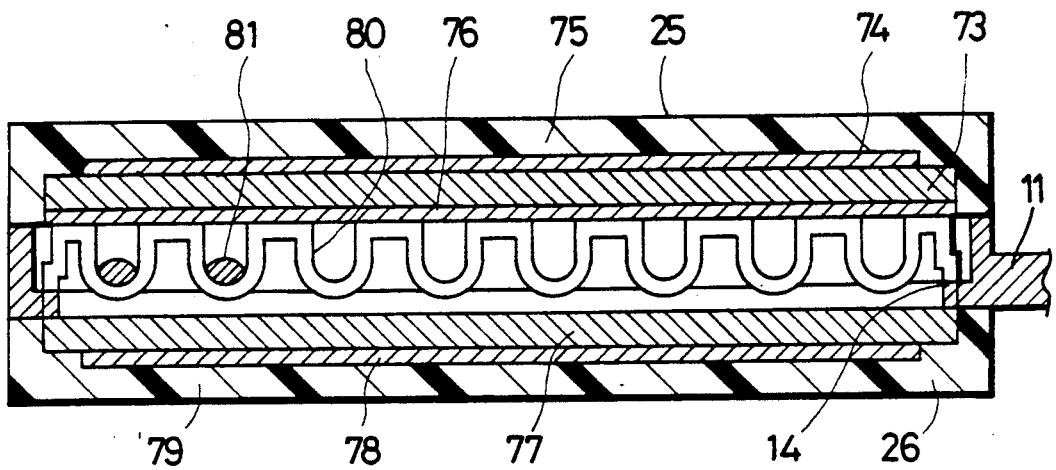
F I G. 11
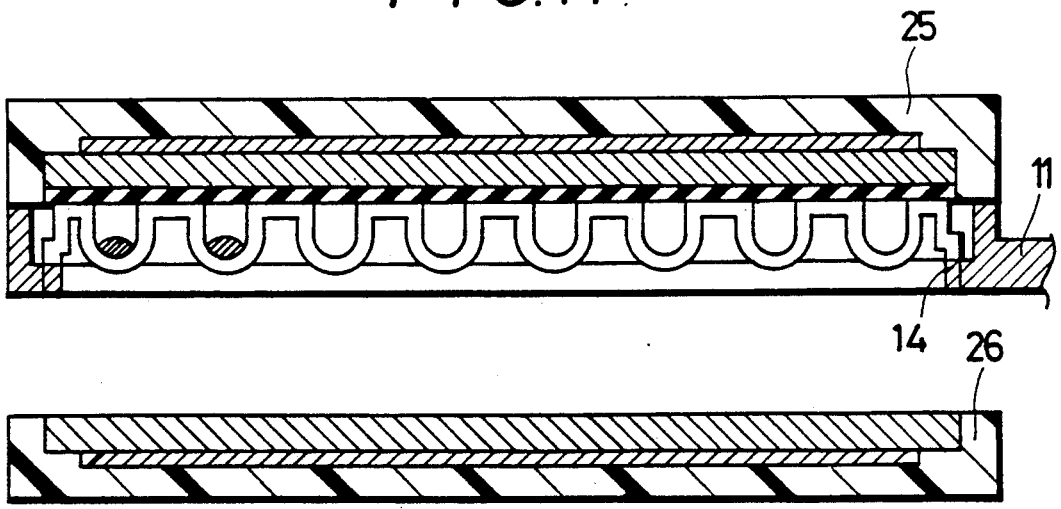

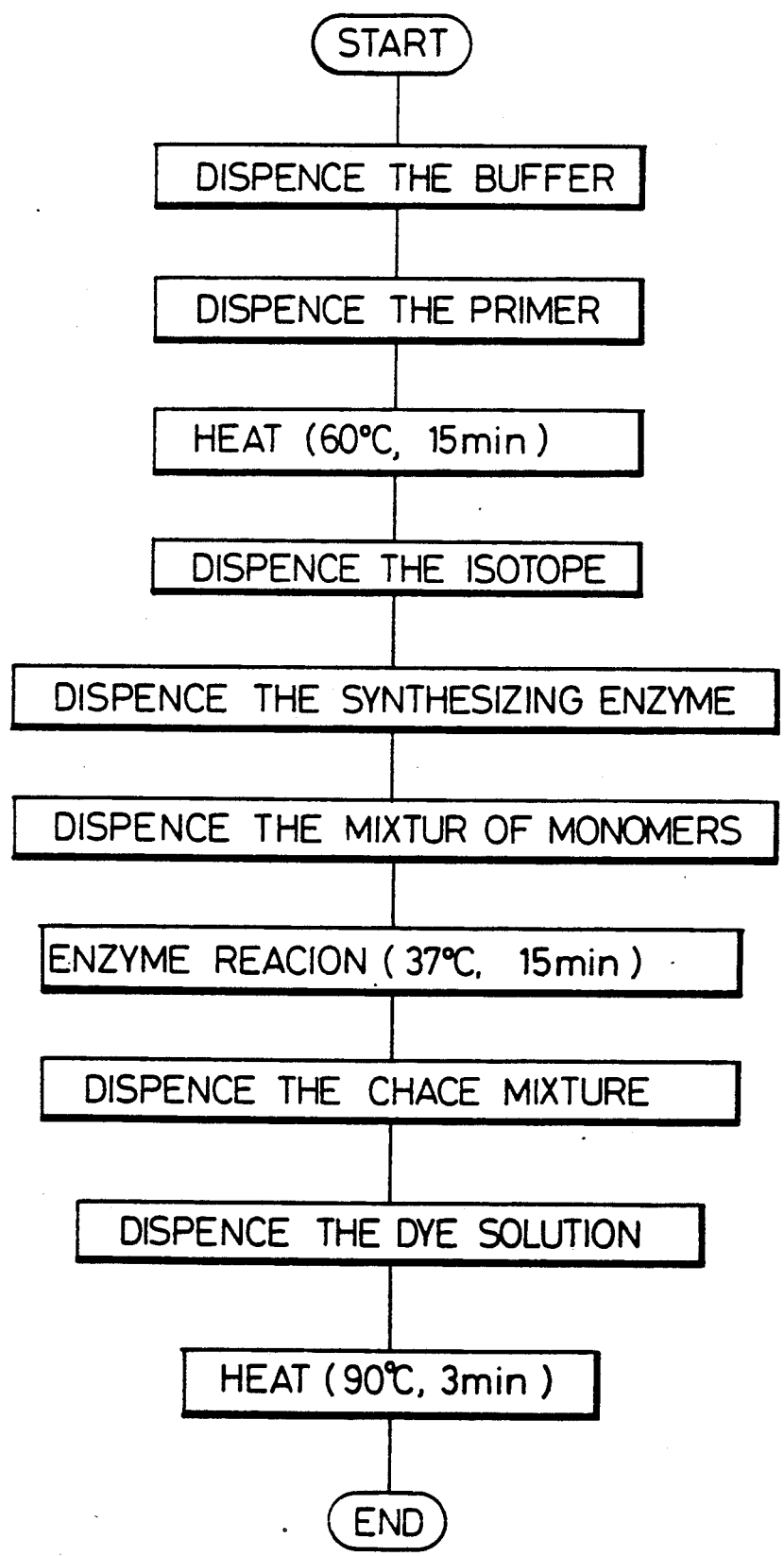

INFINITESIMAL LIQUID REACTOR

BACKGROUND OF THE INVENTION

1. Field of the Invention

This invention relates generally to an automatic reactor for automatically carrying out a reaction process in a laboratory or a sample treatment process, more particularly to an automatic infinitesimal liquid reactor which treats infinitesimal liquid samples and reagents with an automated pipetter.

2. Description of the Prior Art

In the biochemical field, many enzyme reaction processes are used to analyze biochemical samples such as protein and nucleic acid in a laboratory.

Such enzyme reaction processes are composed of many repetitions of treating an infinitesimal liquid quantity and thermally treating at a precise temperature. Conventionally, such enzyme reaction processes are carried out manually by laboratory staffs and constitute very tedious work.

In recent years, attempts have been made to carry out sample preparation processes by robots instead of human beings. Experimental instruments, reagents and a robotic arm capable of manipulating sample tubes and syringes are placed on a desk and the robotic arm is controlled so as to carry out the sample preparation processes by manipulating the experimental instruments and reagents. F. H. Zenie, et al., described in detail such a robotic approach to automated sample preparation in the periodical AMERICAN LABORATORY, June 1982, pages 96-104.

In the robotic approach of the prior art, the experimental instruments and reagents are disposed in a single plane, thus requiring a large space for the installation. Accordingly, once installed, the robot system occupies almost completely the space on a table top, leaving no space for other tasks and apparatus. Further, reagents such as enzymes which are unstable at room temperature are not allowed to remain in the work area, so that the available process and reagents are limited, and the system is unsuitable particularly for treatment of enzymes and like.

SUMMARY OF THE INVENTION

It is therefore a primary object of the invention to provide an automatic infinitesimal liquid reactor requiring a small space for installation on a work surface.

It is another object of the invention to provide an automatic infinitesimal liquid reactor capable of retaining unstable reagents such as enzymes therein for long periods.

It is a further object of the invention to provide an automatic infinitesimal liquid reactor whose operation is very simple and easy.

To accomplish the aforementioned objects, the invention comprises a sample cell, a first stage on which the sample cell is placed, a second stage superposed on the first stage with a reagent stand in which a plurality of reagent cells are housed placed thereon, means for sliding a first stage, means for sliding the second stage, pipetting means for sucking and discharging a reagent stored in the reagent cells, means for sliding at least pipetting ends of pipetting means vertically to the direction in which the first and second stages slide.

According to the aforementioned construction, the second stage is moved, a suction end is disposed on the reagent cell, the pipetting end is moved, and a reagent is sucked by pipetting means. Then, continuously, the pipetting end is moved, the second stage is housed, and the first stage is moved. In this case, the pipetting end is disposed on the sample cell on the first stage. Then, the pipetting end is moved, and the reagent is dispensed into the sample cell by means of pipetting means.

BRIEF DESCRIPTION OF THE DRAWINGS

FIG. 10 is a cross-sectional view of an upper heater and lower heater of the reactor according to the invention in a state where a microplate is sandwiched between the two heaters.

FIG. 11 is a view similar to that of FIG. 10 in the state where the lower heater is detached from the microplate.

FIG. 12 is a flow diagram illustrating one process carried out in the reactor according to the invention.

DESCRIPTION OF THE PREFERRED EMBODIMENTS

Figure 1:
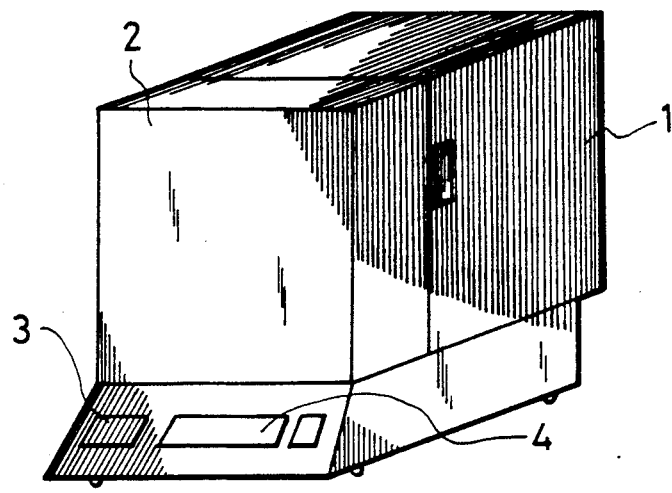
FIG. 1 is a perspective view of the exterior of an infinitesimal liquid reactor according to the invention.

An embodiment of the invention will now be described with reference to the accompanying drawings. FIG. 1 is a perspective view of an infinitesimal liquid reactor according to the invention. The reactor can be placed on a table or desk for use and includes an enclosure 1 having dimensions equivalent to those of an analyzing balance used normally in a laboratory, and a cover 2 closing the entire front of enclosure 1. Cover 2 is preferably made of transparent or translucent acrylic resin or the like to permit viewing of the interior of enclosure 1. However, cover 2 is preferably of a material which shades radiant energy ($\beta$ rays, for example) and the like preferably, thus enhancing safety when a radiated sample is used. A display 3 and a keyboard 4 are provided on a lower portion of the front of enclosure 1.

Figure 2:
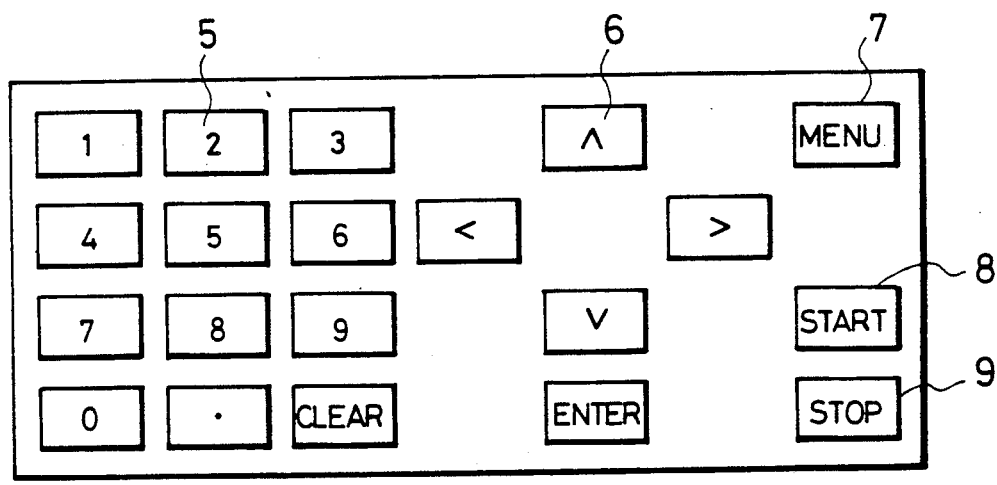
FIG. 2 is a pictorial view of a keyboard of the reactor of FIG. 1.
Figure 3:
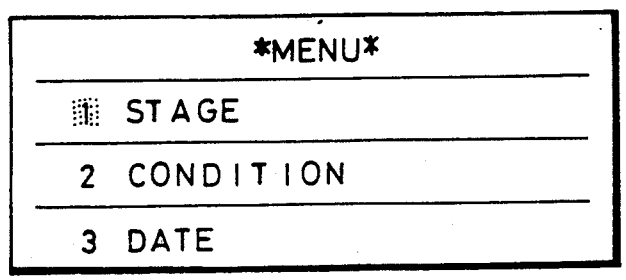
FIG. 3 is a pictorial view of a display of the reactor of FIG. 1.

One example of keyboard 4 is shown in FIG. 2. Keyboard 4 comprises digit keys 0 to 9 for inputting number of samples, conditions and other parameters, cursor keys 6 for shifting a cursor indicated on display 3, a menu key 7 for selecting an input mode, a start key 8 and a stop key 9 for controlling operation of the reactor. FIG. 3 shows a menu indicated as one example on the display 3. The cursor flickers on "1" in FIG. 3.

Figure 4:
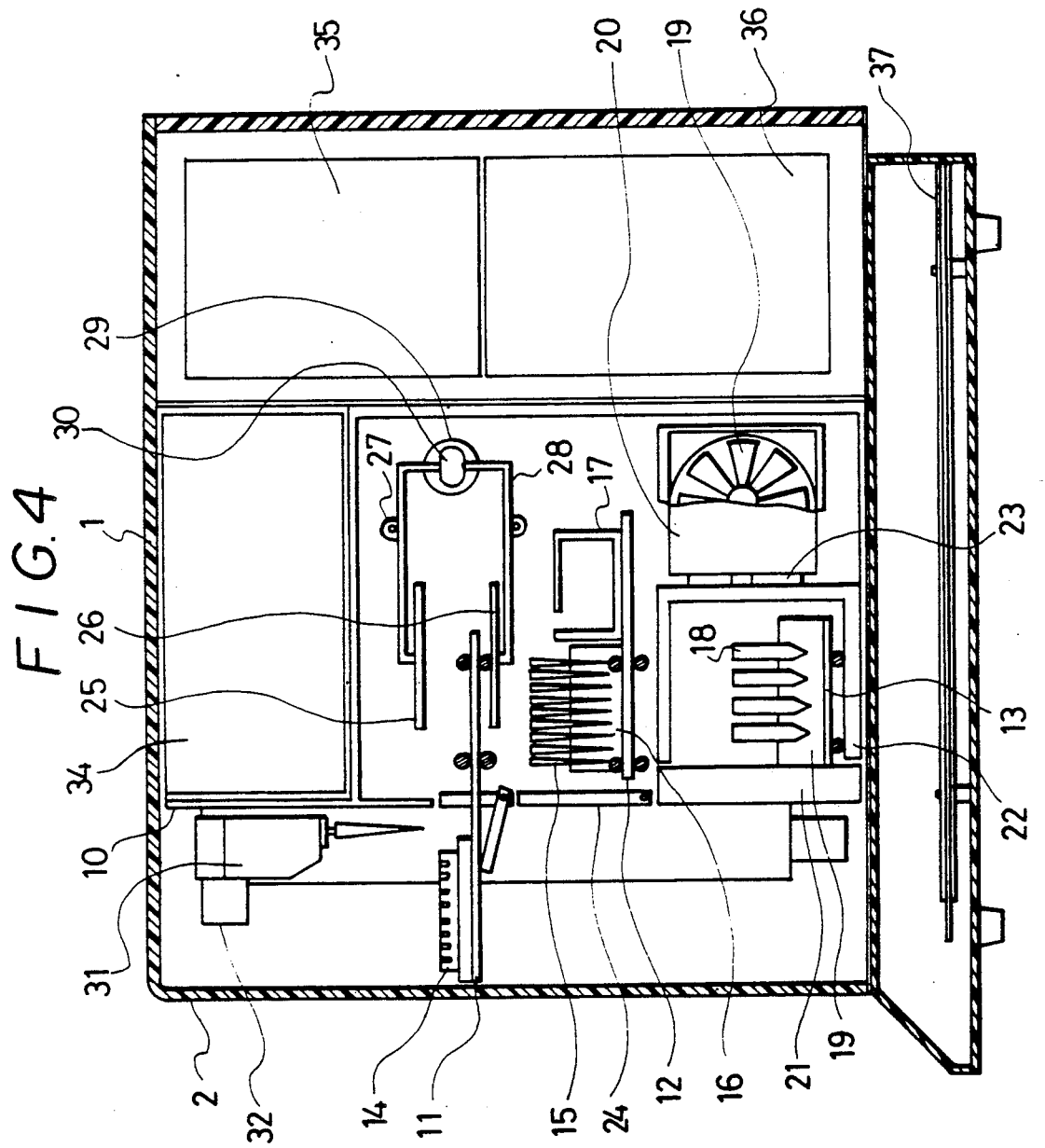
FIG. 4 is a simplified cross-sectional side view of the infinitesimal liquid reactor according to the invention.

FIG. 4 shows a transverse cross section of the reactor. Operating parts of the reactor comprise roughly a reagent dispensing part provided at the front, and a temperature treating part and a containing part partitioned from the dispensing part by a panel 10.

The reactor has three stages which are slidably mounted. These are a plate stage 11, a tip stage 12, and a reagent stage 13, arranged in that order from the top.

A microplate 14 having a plurality of small recesses is mounted on plate stage 11. A tip stand 16 holding a plurality of tips 15 thereon and a waste tip cell 17 for receiving used tips 15 are mounted on tip stage 12. A reagent stand 19 with a plurality of reagent cells or receptacles 18 disposed thereon is mounted on reagent stage 13, and a reagent door 21 is mounted in front of stand 19. The reagent cells 18 are cooled down by a thermomodule 23 mounted between a cooling fin 20 provided with a fan 19 and a cooler 22 sealed by reagent door 21.

The arrangement is such that plate stage 11, tip stage 12 and reagent stage 13 can each be slid between the reagent dispensing part and the temperature treating and containing part by sliding mechanisms which are not indicated. Then, to provide a complete partition when the plate stage 11 and the tip stage 12 shift to the temperature treating and containing part, a closeable door 24 is provided for each of them.

An upper heater 25 and a lower heater 26 are provided in the temperature treating and containing part vertically spaced at positions corresponding to the location of microplate 14 at the time when plate stage 11 is contained in the temperature treating and containing part.

The upper heater 25 and the lower heater 26 are mounted so as to move vertically toward and away from one another on arms 28 around supporting pivot points 27. A cam 30 mounted on cam driving motor 29 is provided so as to drive the upper heater 25 and the lower heater 26 vertically via arms 28. Then the cam 30 drives either upper heater 25 or lower heater 26 only through a rotational angle.

In the reagent dispensing part, a pipetter, or pipette unit, 31 is mounted on a horizontal guide rail 32 to be slidable in a horizontal direction perpendicular to the plane of FIG. 4, and horizontal guide rail 32 is mounted on a vertical guide rail 33 so as to be slidable in the vertical direction. As an electric system for controlling driving and temperature processing operations, a motor drive unit 34 is provided in the upper portion of the reactor, a power unit 35 and a control unit 36 are provided at the rear portion, and a temperature regulating unit 37 is provided at the bottom portion.

Figure 5:
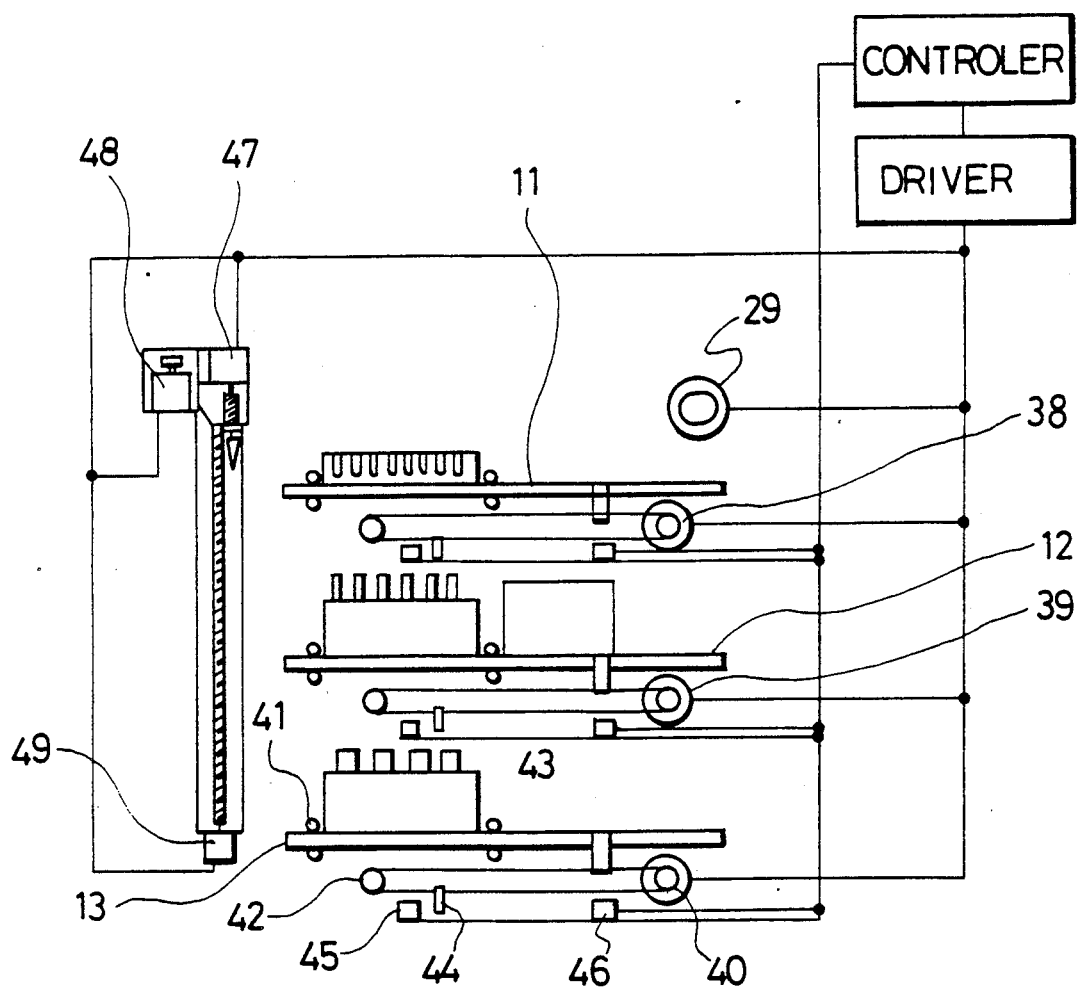
FIG. 5 is a schematic side view of a driving system of the infinitesimal liquid reactor according to the invention.

FIG. 5 is a block diagram of the driving system for the apparatus of FIG. 4. Plate stage 11, tip stage 12 and reagent stage 13 are slid on respective guide rollers 41 by a plate stage motor 38, a tip stage motor 39 and a reagent stage motor 40, respectively, each acting through a respective drive belt 43 guided around a pulley 42. A shutter 44 is mounted on each belt 43, and end points in the travel of the respective stage are detected by shutter 44 blocking an origin sensor 45 or a limit sensor 46 which are photo-interrupting type photosensors.

Figure 6:
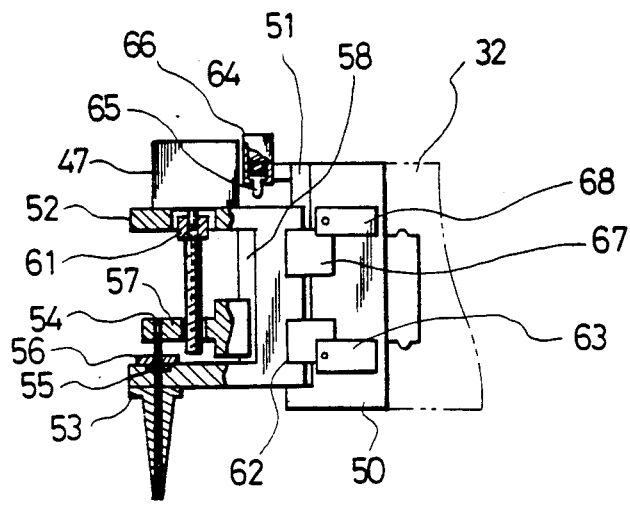
FIG. 6 is a cross-sectional detail view of a part of a reactor according to the invention.

Referring simultaneously to FIG. 6, pipetter 31 is operated by a pipetter motor 47 to draw in or discharge a liquid, and is slid along the horizontal guide rail 32 by a horizontal drive motor 48. Horizontal guide rail 32 is slid along vertical shaft guide rail 33 by a vertical drive motor 49. The cam driving motor 29, plate stage motor 38, tip stage motor 39, reagent stage motor 40, pipetter motor 47, horizontal drive motor 48 and vertical drive motor 49 are driven by a driver according to signals from a controller. Each sensor signal from sensors 45 and 46 is inputted to the controller for processing.

FIG. 6 is a sectional view of one embodiment of the pipetter. The pipetter comprises: a movable base 50 slidably mounted on horizontal guide rail 32, and having a guide rail 51 mounted on another face; a pipetter frame 52 slidably mounted on guide rail 51; a needle guide 53 fixed on pipetter frame 52 for frictionally holding a tip 15 thereon and having a longitudinal passage; a needle 54 extending into the passage in needle guide 53 to serve as a piston or plunger when a tip 15 is in place on guide 53; an 0-ring 55 for sealing the space between pipetter frame 52 and needle 54; a plate 56 for retaining 0-ring 55; a movable bed 57 for moving needle 54 axially of the tip and having a threaded bore; a vertical guide rail 58 fixed on pipetter frame 52 for guiding a slide forming part of bed 57; a feed screw 59 engaging the bore in bed 57 and rotatable for moving bed 57 along rail 58; pipetter motor 47 fixed on pipetter frame 52 for rotating feed screw 59; a coupling 61 transferring a turning force from pipetter motor 47 to feed screw 59; a first sensor plate 62 for detecting that needle guide 53 has come in contact with a tip or a bottom or a reagent cell in cooperation with a first photosensor 63 provided on base 50; a pressuring mechanism 64 fixed on base 50 including a push pin 65 for contacting the pipetter frame 52 and a spring 66 for applying a pressure to push pin 65; and a second sensor plate 67 fixed on pipetter frame 52 for detecting, in cooperation with a second photosensor 68 fixed on base 50, that pipetter frame 52 has been lifted up by a predetermined quantity. In FIG. 6, as well as FIGS. 7 and 8 to be described below, the point of connection of mechanism 64 to base 50 is hidden by rail 51.

Operations will be described next.

Figure 7:
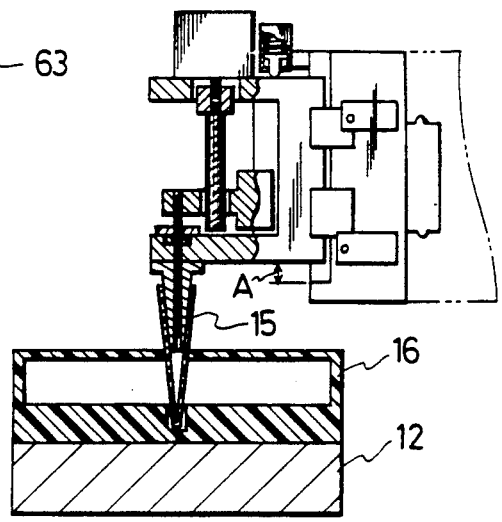
FIG. 7 is a view similar to that of FIG. 6.

FIG. 7 illustrates the relationship between the pipetter 31 and a tip stand 16 when a tip 15 is to be installed on needle guide 53. First, with stage 12 extended, horizontal drive motor 48 is driven so as to move needle guide 53 of pipetter 31 above a tip 15. Vertical drive motor 49 is then driven so as to move pipetter 31 downward until needle guide 53 is inserted into tip 15 and comes in contact with it.

As pipetter 31 continues to move downwardly, frame 52 will slide upwardly relative to moving base 50 until first sensor plate 62 moves to unblock first photosensor 63. Thus, first photosensor 63 is actuated to detect contact of tip 15 with needle guide 53.

Further downward movement of pipetter 31 brings frame 52 into contact with pressuring mechanism 64 to that insertion of guide 53 into tip 15 is effected by a pressure proportional to the distance through which frame 52 descends after tip 15 comes in contact with needle guide 53. When a selected pressure has been reached, that is, after descent by a predetermined distance, A, second sensor plate 67 blocks second photosensor 68, providing an indication that guide 53 has been inserted into tip 15 with a predetermined pressure. This indication causes vertical shaft motor 49 to stop. When the insertion operation is completed, vertical shaft motor 49 is then rotated in the opposite direction to raise pipettes 31 and the operation for insertion ends.

By this operation, an inserted state of the needle guide 53 and the tip 15 may be kept uniform irrespective of variations in tip size and other errors. Further, a load more than necessary will never be applied to the pipetter and the motor.

Figure 8:
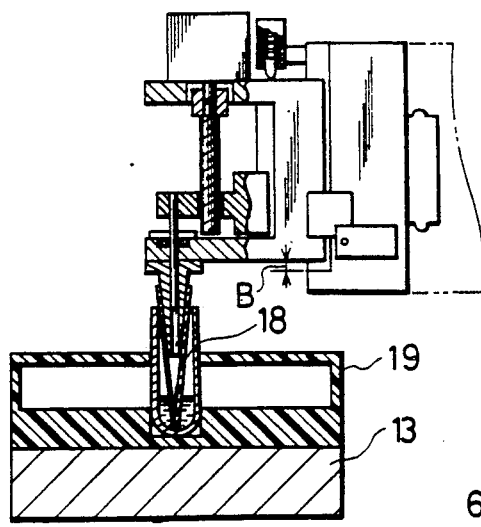
FIG. 8 is a view similar to that of FIG. 6 showing the device of FIG. 6 in position to draw in a reagent.

FIG. 8 illustrates the relationship between the pipetter 31 and a reagent cell 18 at the time of inserting tip 15 into reagent cell 18. First, horizontal drive motor 48 is driven so as to move the tip 15 of pipetter 31 above reagent cell 18.

The vertical drive motor 49 is then driven so as to move pipetter 31 downward until the unblocking of first photosensor 63 indicates that tip 15 has made contact with the bottom of reagent cell 18. This indication causes motor 49 to stop and simultaneously causes pipetter motor 47 to start in a direction which displaces needle 54 upwardly. Therefore, the pressure in the space within the tip becomes less than atmospheric pressure, and a predetermined quantity of reagent in cell 18 is drawn into tip 15. When the drawing in of fluid ends, vertical drive motor 49 is driven so as to move the pipetter upwards.

Then, to perform a discharge operation, needle 54 is driven downwardly by reversing motor 47.

Next described in detail is a mechanism for detecting contact of the tip with a cell. Pipetter frame 52 and the guide rail 51 are in contact with each other. In the state shown in FIG. 6, pipetter frame 52 is in contact with a projection of moving base 50 under the influence of gravity. The first photosensor 63 fixed on moving base 50 is capable of discriminating whether or not an object, i.e., plate 62, is present between its light emitting part and light receiving part. First sensor plate 62 fixed on pipetter frame 52 is present between the light emitting part and light receiving part of first photosensor 63 when frame 52 is in contact with the projection of base 50. Then, if the nose portion of tip 15 comes in contact with the bottom of a reagent cell 18, frame 52 cannot move downward any further. However, since frame 52 is slidable relative to moving base 50, base 50 continues moving downwardly until vertical drive motor 49 stops. This movement continues until frame 52 is displaced relative to base 50 by a distance B, as shown in FIG. 8. At this point, plate 62 moves out of the light path of first photosensor 63, producing a signal which is applied to a controller (not shown), which then issues a rotation stop command to vertical drive motor 49. Motor 49 then halts and the nose portion of tip 15 contacts bottom portion of reagent cell 18 with a pressure determined by the weight of pipetter frame 52 and other parts incidental thereto.

Figure 9:
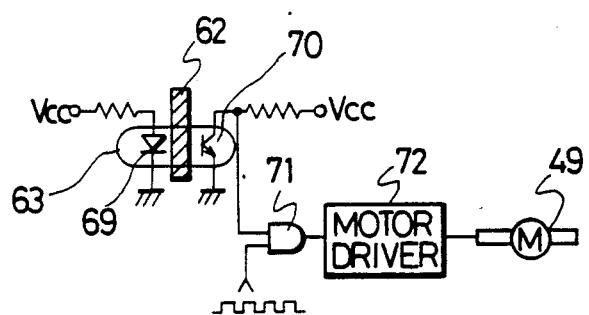
FIG. 9 is a schematic diagram of the circuit photosensor used in the structure of FIG. 7.

FIG. 9 relates to two kinds of electrical processes associated with two kinds of positional relations between sensor plate 62 and first photosensor 63. Photosensor 63 is here composed of an LED 69 and a phototransistor 70. A current does not flow between collector and emitter of phototransistor 70 when the gap between LED 69 and phototransistor 70 is blocked by plate 62. Therefore, one input voltage to a two-input AND element 71 is Vcc, corresponding to a logic "1", so that a motor drive pulse signal which is applied to the other input of element 71 appears at the output thereof, and that signal drives motor 49 through a motor driver 72.

On the other hand, when the path between LED 69 and phototransistor 70 is unblocked, a current flows between the collector and emitter of phototransistor 70, so that the one input voltage to AND element 71 will be at ground level, or logic "0", therefore the output becomes a direct current regardless of the other input, and hence a drive signal is not inputted to the motor. As described, to move pipettes 31 down in order to introduce tip 15 into a cell 18, operation of motor 49 is controlled according to whether or not the path between LED 69 and phototransistor 70 is interrupted. This control procedure allows a fixed positional relation to be established between the tip nose portion and reagent cell 18 irrespective of the shape of the reagent cells and variations in the position of tip 15 on guide 53. Further, the purpose of contact of tip 15 with cell 18 is to prevent liquid from mixing in, thereby ensuring precise discharge or intake. In other words, liquid will flow only in the direction determined by movement of needle 54.

As shown in FIGS. 10 and 11, upper heater 25 is structured such that an upper heating element 74 is disposed directly on the upper surface of an upper soaking plate 73. Plate 73 and element 74 are covered with a body of insulating material 75 and a plate 76 of an elastic and heat conductive material, like rubber, is mounted on the lower surface of plate 73. On the other hand, lower heater 26 comprises a lower heating element 78 tightly secured to the lower surface of a lower soaking plate 77, and a body of insulating material 79 covering the bottom of plate 77 and element 78.

FIG. 10 shows a state where a microplate 14 mounted on plate stage 11 is sandwiched between upper heater 25 and lower heater 26 in order to be heated. In this case, since upper heater 25 and lower heater 26 are controlled to be the same set temperature, the vertical temperature gradient between the two heaters can be minimized, and the precision and accuracy with which temperature of a liquid in microplate 14 is controlled can be enhanced. Further, each well 80 is covered by elastic plate 76 on top of microplate 14 to be sealed thereby raising the ambient pressure of the space in well 80. Therefore evaporation of liquid 81 in well 80 can be decreased.

FIG. 11 shows a state where lower heater 26 is detached from the lower surface of microplate 14 to permit cooling while the upper surface of microplate 14 is pushed against upper heater plate 25. As described hereinbefore, cooling in the configuration shown in FIG. 11 occurs from a condition in which heater 25, microplate 14 and lower heater 26 are heated almost to the same temperature. Accordingly, the cooling rate of liquid in microplate 14 is higher than the cooling rate of upper heater 25, so that liquid 81 which has vaporized into the space in a well 80 can be cooled without condensing on the surface of plate 76. Then, a mechanism for positional control of upper heater 25, microplate 14 and lower heater 26 is provided by cam 30.

As described above, this heating mechanism is effective for enhancing the precision and accuracy of the temperature control of microplate 14 by sandwiching and heating the microplate between the upper heating plate and the lower heating plate. This mechanism is also effective in minimizing any loss of liquid from a sample in the microplate after heating is over and the lower heating plate is removed to permit microplate 14 to be cooled via its lower surface.

FIG. 12 shows an example of a process carried out in the reactor. The example indicates an enzyme reaction process for analyzing DNA base sequence according to a method of Sanger, et al. (Sanger, F., Nicklen, S. and Coulson, A. R., "DNA Sequencing with Chain Terminating Inhibitors", *Proc Natl. Acad. Sci* USA 74, 5463–5467 (1977)). The process is started by setting the microplate 14 with samples in the recesses thereof on plate stage 11. Door 24 is opened and tip stage 12 is propelled to the dispensing part. Next, pipetter 31 descends along vertical shaft guide rail 33, and a tip 15 is installed. Pipetter 31 is lifted and tip stage 12 is returned to the containing part. Reagent stage 13 is propelled into the dispensing part, and pipetter 31 is moved downward to withdraw buffer solution from a reagent cell 18. Then, pipetter 31 is moved upward, reagent stage 13 is returned to the containing part, and plate stage 11 is drawn out to the reagent dispensing part. Pipetter 31 is then lowered until it comes in contact with the bottom of a recession 80 in plate 14. While lifting pipetter 31 slowly, and moving plate 14, motor 47 is driven to discharge an infinitesimal quantity of liquid successively into several recesses of microplate 14. Plate stage 11 is returned to the containing part, tip stage 12 is drawn out to the reagent dispensing part, and the tip 15 presently on pipetter 31 is caught on waste tip cell 17 and is detached into waste tip cell 17.

A primer solution is then dispensed into microplate 14 through a similar operation.

Next, plate stage 11 is returned to the containing part, upper heater 25 and lower heater 26 are driven by cam driving motor 29 to sandwich microplate 14 vertically through cam 30 and arm 28 to perform a thermal treatment.

After the thermal treatment applied for a predetermined time (600; 15 min.), cam 30 is rotated to detach microplate 14 from upper heater 25 and lower heater 26, and the next operation ensues. Operations for dispensing isotope, enzyme and heating are carried out as described above.

The last product obtained as above is subjected to electrophoresis and then analyzed.

What is claimed is:

1. An infinitesimal liquid reactor comprising: first and second stages slidably mounted one above the other for movement in a first direction between a storage position and a working position; means connected to said first and second stages for moving each of said first and second stages individually between said storage and working positions; a sample cell carried by said first stage; means carried by said second stage for storing a plurality of reagents; pipetting means for drawing in and discharging a dose of fluid, said pipetting means including an end carrying a replaceable tip defining a space for storing a dose of fluid; displacing means associated with said pipetting means for moving at least said end in a second direction transverse to the first direction of movement of said first and second stages; and cooling means disposed for cooling down said reagent storage means, wherein said displacing means comprise: a first movable member; driving means for moving said first movable member in the second direction; a second movable member mounted on said first movable member to be slidable relative to said first movable member in the second direction, said second movable member carrying at least said end of said pipetting means; detecting means associated with said second movable member for producing an output signal when said second movable member has a given position relative to said first movable member; and control means coupled to said detecting means for halting movement of said first movable member in response to the appearance of the output signal.

2. A liquid reactor as defined in claim 1 further comprising a third stage disposed above said second stage and having a tip stand carrying a plurality of tips for attachment to said end, the means connected for moving said third stage.

3. An infinitesimal liquid reactor comprising: first and second stages slidably mounted one above the other for movement in a first direction between a storage position and a working position; means connected to said first and second stages for moving each of said first and second stages individually between said storage and working positions; a sample cell carried by said first stage; means carried by said second stage for storing a plurality of reagents; pipetting means for drawing in and discharging a dose of fluid, said pipetting means including an end carrying a replaceable tip defining a space for storing a dose of fluid; displacing means associated with said pipetting means for moving at least said end in a second direction transverse to the first direction of movement of said first and second stages; a third stage disposed above said first stage and having a tip stand carrying a plurality of tips for attachment to said end; and means connected to said third stage for moving said third stage, wherein said displacing means comprise: a first movable member; driving means for moving said first movable member in the second direction; a second movable member mounted on said first movable member to be slidably relative to said first movable member in the second direction, said second movable member carrying at least said end of said pipetting means; propelling means connected for moving said second movable member relative to said first movable member; detecting means connected to detecting the application of a predetermined pressure to said second movable member; and control means responsive to said detecting means for halting movement of said first movable member in response to detection of the predetermined pressure by said detecting means.

4. An infinitesimal liquid reactor comprising: first and second stages slidably mounted one above the other for movement in a first direction between a storage position and a working position; means connected to said first and second stages for moving each of said first and second stages individually between said storage and working positions; a sample cell carried by said first stage; means carried by said second stage for storing a plurality of reagents; pipetting means for drawing in and discharging a dose of fluid, said pipetting means including an end carrying a replaceable tip defining a space for storing a dose of fluid; displacing means associated with said pipetting means for moving at least said end in a second direction transverse to the first direction of movement of said first and second stages; and heating means for heating and retaining said sample cell on said first stage, wherein said heating means comprises: an upper heating plate for heating an upper surface of said sample cell; a lower heating plate for heating a lower surface of said sample cell; first contacting means for bringing said upper heating plate into contact with the upper surface of said sample cell; and second contacting means for brining said lower heating plate into contact with the lower surface of said sample cell.

5. A liquid reactor as defined in claim 4 further comprising a controller connected for controlling said first contacting means and second contacting means in order to first sandwich said sample cell for heating between said upper heating plate and said lower heating plate, and to then detach said lower heating plate from the lower surface of said sample cell for cooling, while said upper heating plate continues to be pushed against the upper surface of sample cell.

6. A liquid reactor as defined in claim 1 further comprising:

means defining a reagent dispensing station containing said pipetting means and in which said first and second stages are located when in their working position;

means defining a temperature treating station spaced horizontally from said reagent dispensing station and in which said first and second stages are located when in their storage position; and thermal treating means disposed in said temperature treating station for treating a material in said sample cell when said first stage is in the storage position.

* * * * *